(12) United States Patent
Jang et al.

(10) Patent No.: US 8,480,578 B2
(45) Date of Patent: Jul. 9, 2013

(54) SKIN MOISTURE CONTENT MEASURING APPARATUS FOR REDUCING POWER CONSUMPTION

(75) Inventors: Woo Young Jang, Seoul (KR); Kun Soo Shin, Seongnam-si (KR); Hong Sig Kim, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1508 days.

(21) Appl. No.: 12/010,204

(22) Filed: Jan. 22, 2008

(65) Prior Publication Data

US 2008/0177198 A1    Jul. 24, 2008

(30) Foreign Application Priority Data

Jan. 22, 2007  (KR) .................. 10-2007-0006677

(51) Int. Cl.
*A61B 5/00* (2006.01)

(52) U.S. Cl.
USPC .......................................... 600/306; 600/307

(58) Field of Classification Search
USPC ............................... 600/306–307, 547; 73/73
See application file for complete search history.

(56) References Cited

U.S. PATENT DOCUMENTS

| | | | | |
|---|---|---|---|---|
| 4,013,065 A | * | 3/1977 | Copeland et al. | 600/306 |
| 4,275,743 A | * | 6/1981 | Hjort | 600/544 |
| 5,353,802 A | * | 10/1994 | Ollmar | 600/547 |
| 5,738,107 A | * | 4/1998 | Martinsen et al. | 600/547 |
| 6,370,426 B1 | | 4/2002 | Campbell et al. | |
| 7,753,846 B2 | * | 7/2010 | Park et al. | 600/307 |
| 2003/0222662 A1 | * | 12/2003 | Geisel | 324/664 |
| 2004/0063152 A1 | * | 4/2004 | Gumbrecht et al. | 435/7.1 |

FOREIGN PATENT DOCUMENTS

| | | |
|---|---|---|
| JP | 60-63039 | 4/1985 |
| JP | 2001-187025 | 7/2001 |
| JP | 2002-90298 | 3/2002 |
| JP | 2002-224049 | 8/2002 |
| KR | 10-2004-0004216 | 1/2004 |
| KR | 10-2005-0083197 | 8/2005 |
| KR | 10-2005-0118876 | 12/2005 |
| KR | 10-2006-0062263 | 6/2006 |
| KR | 1020060069011 | 6/2006 |
| KR | 10-2006-0082852 | 7/2006 |
| KR | 10-0634544 | 10/2006 |
| KR | 1020080016339 | 2/2008 |
| KR | 1020080017832 | 2/2008 |
| WO | WO2004/001373 A2 | 12/2003 |
| WO | WO2005/006968 A1 | 1/2005 |
| WO | WO2005/015163 A2 | 2/2005 |
| WO | WO2005/018443 A1 | 3/2005 |

* cited by examiner

*Primary Examiner* — Patricia Mallari
*Assistant Examiner* — Tiffany Weston
(74) *Attorney, Agent, or Firm* — Staas & Halsey LLP

(57) ABSTRACT

An apparatus to measure skin moisture content, the apparatus including: an electrode unit comprising a reference (R) electrode, a current (C) electrode, and a measuring (M) electrode; an operational amplifier having an inverting input terminal connect with the R electrode, and having an output terminal connect with the C electrode; a first switch connecting the R electrode and the C electrode, and releasing a connection between the R electrode and the C electrode when the electrode unit contacts with the skin of a user; and a microcontroller controlling the connection between the R electrode and the C electrode via the first switch is provided.

8 Claims, 8 Drawing Sheets

FIG. 8

SKIN MOISTURE CONTENT MEASURING APPARATUS FOR REDUCING POWER CONSUMPTION

CROSS-REFERENCE TO RELATED APPLICATIONS

This application claims the benefit of Korean Patent Application No. 10-2007-0006677, filed on Jan. 22, 2007, in the Korean Intellectual Property Office, the disclosure of which is incorporated herein by reference.

BACKGROUND OF THE INVENTION

1. Field of the Invention

The present invention relates to an apparatus to measure skin moisture content, which can reduce power consumption in a measurement standby mode, and more particularly, to an apparatus for measuring skin moisture content, which can connect a reference (R) electrode and a current (C) electrode in a measurement standby mode, and also can release the connection between the R electrode and the C electrode while the skin moisture content is measured from the skin of a user, and thereby can reduce the consumption of power spent before an electrode contacts with the skin of a user.

2. Description of the Related Art

As many people become interested in beauty, an interest in skin care has also increased. A desire for a healthy skin affects not only beauty-related businesses, but also affects the growth of medical-related businesses since people need to protect their skin from ultraviolet rays that have become stronger due to the destruction of the ozone layer, and various types of pollutions.

Skin is an organ of the integumentary system made up of multiple layers of epithelial tissues. Main functions of skin are protecting against pathogens, waterproofing, temperature regulation, insulation, and the like. One of the most critical elements to enable the proper performance of the functions of skin is moisture content in a stratum corneum. The moisture content in the stratum corneum is generally called a skin moisture content. When maintaining a particular moisture content in the stratum corneum, it is possible to perform basic functions of skin such as protecting against harmful substances like pathogens, and preventing excessive evaporation of skin moisture.

In view of skin care, the skin moisture content is also considered as an essential element. Accordingly, fundamental to skin care is skin moisture management.

According to a conventional art, an electrical measurement method, an optical measurement method, and a method using a magnetic resonance imaging (MRI) are included in a method of measuring skin moisture content. The electrical measurement method is widely used. More specifically, a method of measuring the skin moisture content by measuring susceptance, i.e. an alternating current (AC) component of admittance, of three electrodes, i.e. a reference (R) electrode, a current (C) electrode, and a measuring (M) electrode, using a sinusoidal wave of low frequency is generally used.

Among skin moisture content measuring apparatuses using the method of measuring susceptance, it is an issue that a portable skin moisture content measuring apparatus utilizes a maximum functionality within a limited power capacity. Specifically, what is important for any type of portable device is to reduce amounts of power consumption.

However, a conventional apparatus to measure skin moisture content consumes greater amounts of power in a measurement standby mode than when the skin moisture content is substantially measured, due to characteristics of an operational amplifier included in the apparatus for measuring skin moisture content. Specifically, when an electrode makes no contact with the skin of a user, an infinite load occurs in an output terminal of the operational amplifier due to a principle of the operational amplifier and thus, theoretically, an infinite amount of current may flow into a C electrode connecting with the output terminal. Accordingly, huge amounts of power may be consumed.

Specifically, when the electrode makes no contact with the skin of the user and thereby the operational amplifier is in an open loop state, an input impendence becomes almost infinite due to characteristics of the operational amplifier. Therefore, current supplied to the operational amplifier becomes zero, and an output impedance also becomes near zero. Accordingly, output current becomes infinite and thus a gain is also converged to infinity. Also, since the output terminal is in an open state, infinite loads appear to be loaded to the output terminal. Accordingly, to drive the infinite loads, the operational amplifier may try to draw a maximum current which can be inputted from a power source, and perform an output.

Specifically, when the electrode makes no contact with the skin, an input of a noninverting input terminal corresponding to +terminal becomes an input oscillation voltage $V_{in}$, and an input of an inverting input terminal corresponding to −terminal becomes a floating state, and thus any voltage $V_x$ may be generated. Also, since the output terminal is in an open loop state without feedback, amplification may be infinitely performed in the output terminal. Therefore, although loads do not substantially occur, infinite loads and a virtual ground may be formed in the floating state. Accordingly, comparatively huge amounts of current may flow into a C electrode until a current control circuit operates in the operational amplifier.

However, when the electrode contacts with the skin of the user, the virtual ground is formed in the M electrode and thus the current flowing into the C electrode changes according to the strength of impedance of the stratum corneum right below the C electrode and the M electrode. In comparison to the measurement standby mode, a comparatively smaller amount of current may flow into the M electrode.

As described above, the conventional apparatus to measure skin moisture content consumes huge amounts of power in the measurement standby mode. Accordingly, there is a need for an apparatus to measure skin moisture content which can reduce power consumption in a measurement standby mode.

SUMMARY OF THE INVENTION

Additional aspects and/or advantages of the invention will be set forth in part in the description which follows and, in part, will be apparent from the description, or may be learned by practice of the invention.

An aspect of the present invention provides an apparatus to measure skin moisture content, which can connect a reference (R) electrode and a current (C) electrode via a switch, and control the switch to connect the R electrode and the C electrode in a standby mode to measure the skin moisture content, and also control the switch to release the connection between the R electrode and the C electrode while the skin moisture content is measured from the skin of a user, and thereby can reduce power consumption in the standby mode.

Another aspect of the present invention also provides an apparatus to measure skin moisture content, which can connect an R electrode and a C electrode via a resistor and thereby can reduce power consumption in a measurement standby mode. In this instance, the resistor has a comparatively greater resistance value in comparison to stratum corneum.

Another aspect of the present invention also provides an apparatus to measure skin moisture content, which can design a member to be opened and closed, so that a conductor of the member may contact with an R electrode and a C electrode and an insulator of the member may contact with an M electrode in a measurement standby mode, and thereby can reduce power consumption. In this instance, the member connects the R electrode and the C electrode via the conductor, and contacts with the M electrode via the insulator.

Another aspect of the present invention also provides an apparatus to measure skin moisture content, which can design an M electrode to have a stepped pulley with respect to an R electrode and a C electrode, and design a member to be opened and closed, so that a conductor of the member may contact with the R electrode and the C electrode in a measurement standby mode, and thereby can reduce power consumption. In this instance, the member connects the R electrode and the C electrode via the conductor.

According to an aspect of the present invention, there is provided an apparatus to measure skin moisture content, the apparatus including: an electrode unit including a reference (R) electrode, a current (C) electrode, and a measuring (M) electrode; an operational amplifier to have an inverting input terminal connect with the R electrode, and having an output terminal connect with the C electrode; a first switch to connect the R electrode and the C electrode, and to release a connection between the R electrode and the C electrode when the electrode unit contacts with the skin of a user; and a microcontroller to control the connection between the R electrode and the C electrode via the first switch.

According to another aspect of the present invention, there is provided an apparatus for measuring skin moisture content, the apparatus including: an electrode unit comprising an R electrode, a C electrode, and an M electrode; an operational amplifier to have an inverting input terminal connect with the R electrode, and having an output terminal connect with the C electrode; and a resistor connecting with the R electrode and the C electrode.

According to still another aspect of the present invention, there is provided an apparatus to measure skin moisture content, the apparatus including: an electrode unit including an R electrode, a C electrode, and an M electrode; an operational amplifier to have an inverting input terminal connect with the R electrode, and to have an output terminal connect with the C electrode; and a member including a conductor contacting with the R electrode and the C electrode, and an insulator contacting with the M electrode.

According to yet another aspect of the present invention, there is provided an apparatus to measure skin moisture content, the apparatus including: an electrode unit including an R electrode, a C electrode, and an M electrode, the M electrode including a stepped pulley with respect to the R electrode and the C electrode; an operational amplifier to have an inverting input terminal connect with the R electrode, and to have an output terminal connect with the C electrode; and a member including a conductor contacting with the R electrode and the C electrode.

Additional aspects, features, and/or advantages of the invention will be set forth in part in the description which follows and, in part, will be apparent from the description, or may be learned by practice of the invention.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION OF THE PREFERRED EMBODIMENTS

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

An apparatus to measure skin moisture content according to the present invention may be embodied as any portable devices, such as a mobile communication terminal, a personal digital assistance (PDA), a portable game device, a Moving Picture Experts Group Audio-Layer 3 (MP3) player, a portable multimedia player (PMP), a Digital Multimedia Broadcasting (DMB) terminal, a notebook, and the like. Specifically, the apparatus to measure skin moisture content may be embodied as a partial configuration of the portable devices or may be independently embodied as a single product, instead of being embodied as the partial configuration of the portable devices.

The apparatus to measure skin moisture content according to the present invention may measure each of skin moisture content by electrically modeling a biological structure of skin. Hereinafter, a measurement principle of measuring the skin moisture content according to electrical modeling of the skin will be described with reference to FIGS. 1 through 3. Also, an apparatus to measure skin moisture content and a method of operating the same according to each exemplary embodiment of the present invention will be described with reference to FIGS. 4 through 6.

Figure 1:
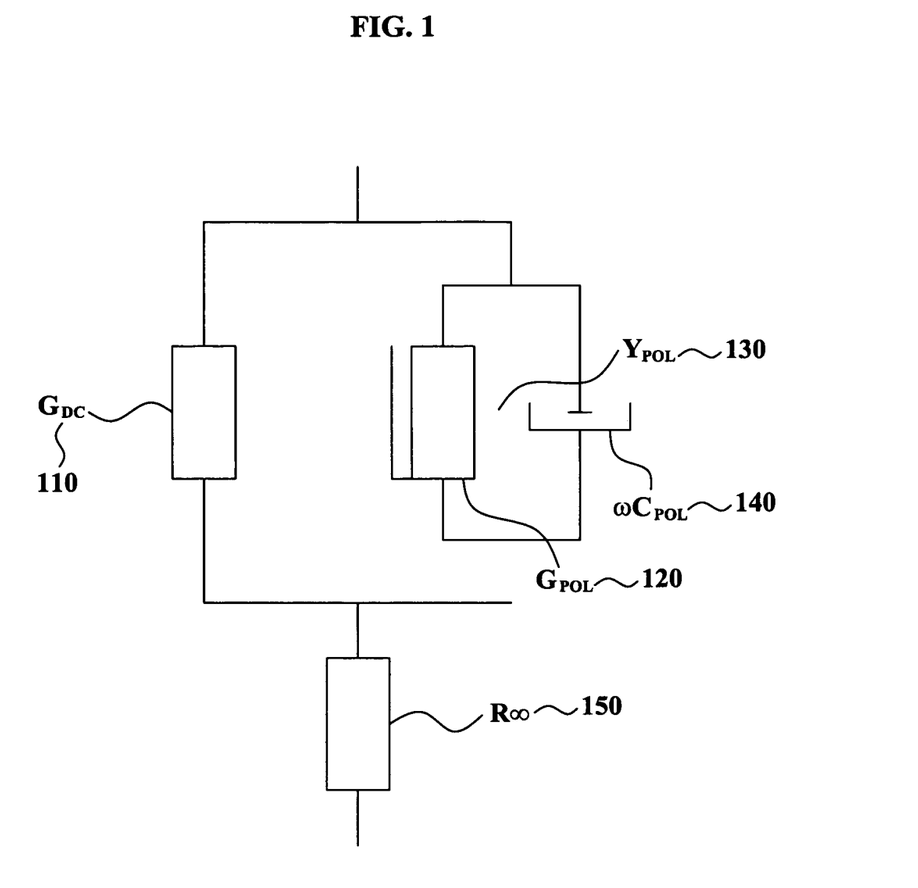
FIG. 1 is a circuit diagram illustrating an electrically modeled biological structure of skin.

To electrically measure the skin moisture content, it is used to electrically model the biological structure of the skin. FIG. 1 illustrates an electrically modeled biological structure of skin by using a Yamamoto-Yamamoto model, 'The measurement principle for evaluating the performance of drugs and cosmetics by skin impedance' in Med. & Biol. Eng. & Comput. 1978. The Yamamoto-Yamamoto model reinterpreted a Cole-Cole model, 'Dispersion and absorption in dielectrics', in J. Soc. Cosmet. Chem. 1941.

In FIG. 1, $G_{DC}$ 110 generally indicates a sweat gland activity of a stratum corneum. $R_\infty$ 150 indicates a value which is acquired by electrically modeling a liable cell from a bottom of a stratum corneum to a dermis. The $R_\infty$ is direct current (DC) dominant, $Y_{POL}$ 130 indicates an admittance component due to a polarizing phenomenon, and is alternating current (AC) dominant. A $\omega C_{POL}$ 140 component is known to model the skin moisture content of the stratum corneum. Accordingly, when measuring the skin moisture content of the stratum corneum, removing an effect of $R_\infty$ 150 and $G_{DC}$ 110 may become an important issue.

To measure only the $\omega C_{POL}$ 140 component, only susceptance which is an AC component of the admittance component is required to be measured. For this, an analog lock-in amplifier may be utilized.

Specifically, $R_\infty$ may be assumed to be a conductor. When a constant voltage signal of a regular frequency, for example, $\omega=2\pi f$, is supplied to a human body by using $R_\infty$ as the conductor, a current, which reacts to an impedance of the stratum corneum, may be measured through the conductor of a liable cell layer. In this instance, the stratum corneum closely attaches to a measurement electrode. The admittance of the stratum corneum of a measured area may be measured by using the current.

A response signal which converts the measured current to a voltage is represented as $$Vsig = |Vsig|\sin(\omega rt + \theta sig) \quad \text{[Equation 1]}$$

Also, an out-of-phase reference signal having a phase difference of 90° to be synchronous with the response signal is represented as $$V_{L\_90} = |V_{L\_90}|\cos(\omega_{L\_90}t + \theta_{ref\_0}) \quad \text{[Equation 2]}$$

In this case, an in-phase reference signal having a phase difference of 0° to be synchronous with the response signal may be represented as, $$V_{L\_0} = |V_{L\_0}|\sin(\omega_{L\_0}t + \theta_{ref\_0}) \quad \text{[Equation 3]}$$

In this instance, when synchronizing the response signal and the reference signal having the phase difference of 90° using a multiplier, a signal may be generated by $$\begin{aligned} V_{PSD} &= |Vsig||V_{L\_90}|\sin(\omega rt + \theta sig)\cos \\ &\quad (\omega_{L\_90}t + \theta_{ref\_90}) \\ &= 1/2|Vsig||V_{L\_90}|\{\sin([\omega r - \omega_{L\_90}]t + \\ &\quad \theta sig - \theta_{ref\_90}) - \sin([\omega r + \omega_{L\_90}]t + \theta sig + \theta_{ref\_90})\} \end{aligned} \quad \text{[Equation 4]}$$

Also, when the signal passes through a low-pass filter (LPF), the AC component is removed from the signal. Accordingly, $V_{PSD}$ becomes '0'.

However, when frequencies of the reference signal and the response signal are identical, i.e. $\omega r = \omega_{L\_90}$, an output of the LPF may be represented as $$Vout\_90 = 1/2|Vsig||V_{L\_90}|\sin(\theta sig - \theta_{ref\_90}) \quad \text{[Equation 5]}$$

Also, when synchronizing the in-phase reference signal and the response signal by a method as described above, it may be given by $$Vout\_0 = 1/2|Vsig||V_{L\_0}|\cos(\theta sig - \theta_{ref\_0}) \quad \text{[Equation 6]}$$

Also, when $|VSig|V_L| = Vout$ and $\theta sig - \theta ref = \theta out$ to simplify the equations with respect to the Vout_90 and Vout_0, it may be arranged by $$V_{PSD\_filtered\_0} = 1/2 Vout \cos(\theta out). \quad \text{[Equation 7]}$$

Figure 2:
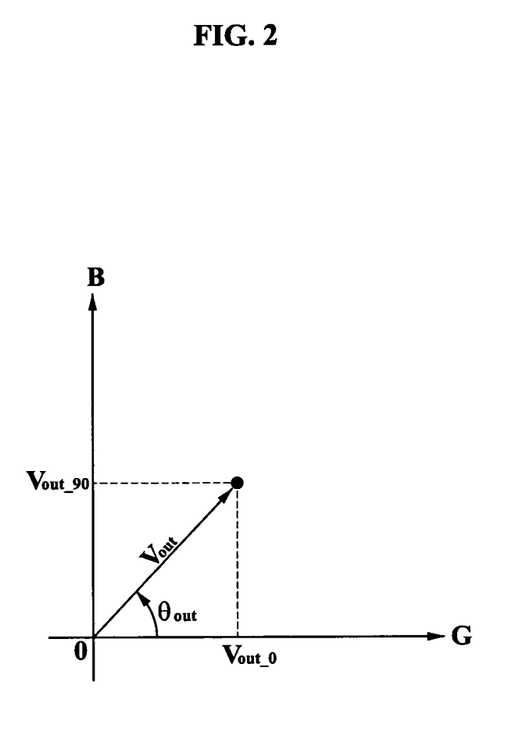
FIG. 2 illustrates a graph of an admittance by a skin moisture content measurement result.

The equations with respect to the Vout_90 and Vout_0, i.e. Equation 5 and Equation 6 designate a conductivity signal which is generated by supplying a constant AC voltage and measuring the current. Accordingly, the admittance is measured. FIG. 2 illustrates a graph of the admittance. In FIG. 2, G designates conductance, and B designates susceptance. When G and an in-phase synchronous signal are combined, G may be measured. When B and a quadrature-phase synchronous signal are combined, B may be measured.

As described above, the skin moisture content may be measured from susceptance that is measured via an out-of-phase signal. In this instance, a conductance component reflects an effect of sweat gland activity of the stratum corneum and thus the conductance component must be eliminated to measure only the skin moisture content. Accordingly, only susceptance may be measured by using an out-of-phase synchronous signal. According to the present exemplary embodiment, it is possible to apply a method of measuring susceptance, which changes according to time, to measure skin moisture content.

Figure 3:
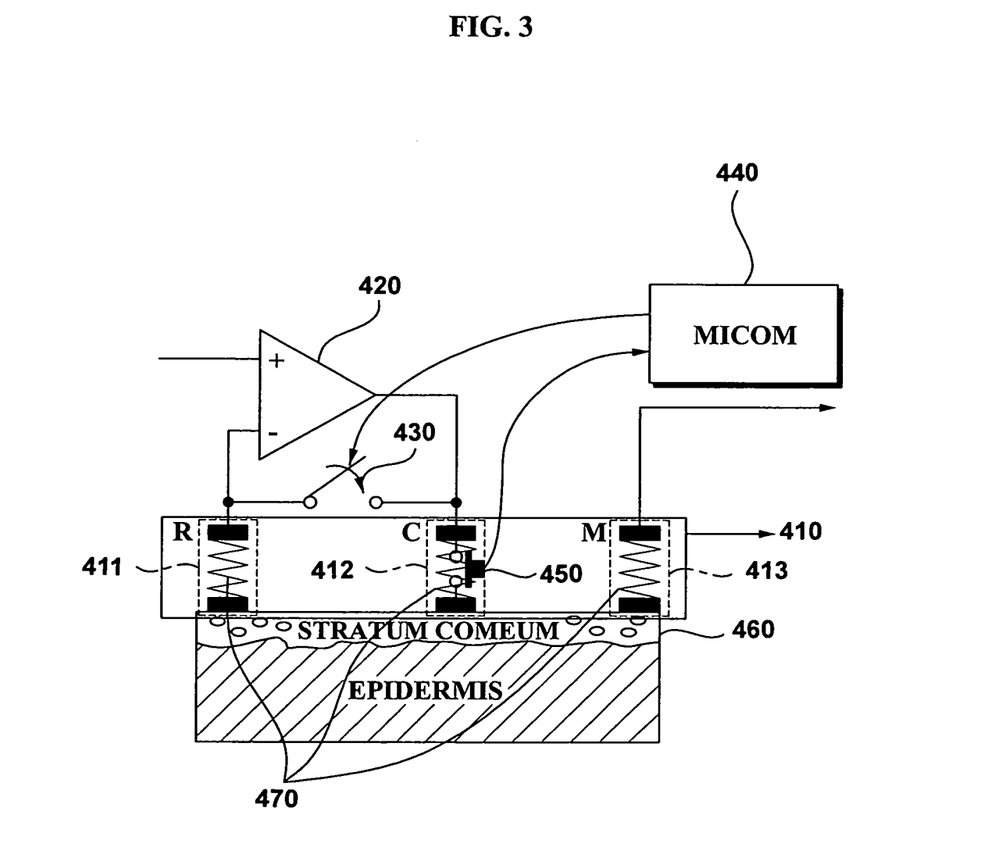
FIG. 3 illustrates a configuration of an apparatus to measure skin moisture content according to a first embodiment of the present invention.

FIG. 3 illustrates a configuration of an apparatus to measure skin moisture content according to a first embodiment of the present invention.

The apparatus to measure skin moisture content according to the present exemplary embodiment includes an electrode unit 410, an operational amplifier 420, a first switch 430, a microcontroller MICOM 440, and a second switch 450.

The electrode unit 410 includes a reference (R) electrode 411, a current (C) electrode 412, and a measuring (M) electrode 413. Specifically, as well-known to those of ordinary skill in the art, the electrode unit 410 may be constructed to include the R electrode 411, the C electrode 412, and the M electrode 413. Also, the electrode unit 410 may be constructed to include any type of electrode that can measure the skin moisture content.

Each of the R electrode 411, the C electrode 412, and the M electrode 413 includes an elastic device 470, respectively. Specifically, each of the R electrode 411, the C electrode 412, and the M electrode 413 may include two electrodes, and the two electrodes may connect with each other via the elastic device 470. Accordingly, when a user applies pressure to measure the skin moisture content while making the electrode unit 410 contact with the skin of the user 460, the elastic device 470 is contracted and thereby the two electrodes, included in each of the R electrode 411, the C electrode 412, and the M electrode 413, may contact with each other.

Also, the C electrode 412 includes the second switch 450. In this instance, the second switch 450 may be embodied as an elastic switch. Specifically, the second switch 450 may be configured to maintain an open state in a measurement standby mode, and to be in a connection status due to a contraction of the elastic device when the user applies the pressure to the electrode unit 410. Specifically, when the second switch 450 is in the connection status, an output terminal of the operational amplifier 420 and the C electrode 412 contacting with the skin of the user 460 may electrically connect with each other.

In this instance, an inverting input terminal of the operational amplifier 420 connects with the R electrode 411, and an output terminal of the operational amplifier 420 connects with the C electrode 412.

The microcontroller 440 controls the connection between the R electrode 411 and the C electrode 412 via the first switch 430, depending on a connection status of the second switch 450. The microcontroller 440 closes the first switch 430, and thereby controls the first switch 430 to connect the R electrode 411 and the C electrode 412 while the connection of the second switch 450 is released. Also, the microcontroller 440 opens the first switch 430 and thereby controls the first switch 430 to release the connection between the R electrode 411 and the C electrode 412 while the connection of the second switch 450 is maintained.

Specifically, when the second switch 450 is opened in a measurement standby mode, the microcontroller 440 controls the first switch 430 to be closed. Also, when the C electrode 412 contacts with the skin of the user 460 and thus the second switch 450 is closed to measure the skin moisture content, the microcontroller 440 controls the first switch 430 to be opened.

As described above, since the microcontroller 440 controls the first switch 430 to be either opened or closed, the R electrode 411 and the C electrode 412 may electrically connect with each other in the measurement standby mode. As the R electrode 411 and the C electrode 412 electrically connect with each other via the first switch 430, the output terminal and the inverting input terminal of the operational amplifier 420 also electrically connect with each other and form a loop. Specifically, current flowing from the output terminal of the operational amplifier 420 into the C electrode 412 is generally streamed to the inverting input terminal of the operational amplifier 420 via the first switch 430 and thus theoretically, no current flow exists. In actuality, only a minute current may flow.

Accordingly, it is possible to reduce power consumption which is caused when huge amounts of current flowing into the C electrode 412 in the measurement standby mode, which occurs in the related art. Also, in this case, an output voltage of the output terminal of the operational amplifier 420 is set to be identical to an input voltage of the inverting input terminal of the operational amplifier 420. Accordingly, it is possible to achieve a stability of circuit in the measurement standby mode.

Also, when the R electrode 411, the C electrode 412, and the M electrode 413 contact with the skin of the user 460 and thus the second switch 450 is closed to measure the skin moisture content, the microcontroller 440 senses the above event, and controls the first switch 430 to be opened. As the first switch 430 is opened, the current outputted from the output terminal of the operational amplifier 420 flows into the C electrode 412. Also, the apparatus for measuring skin moisture content may measure the skin moisture content from the skin of the user 460.

Figure 4:
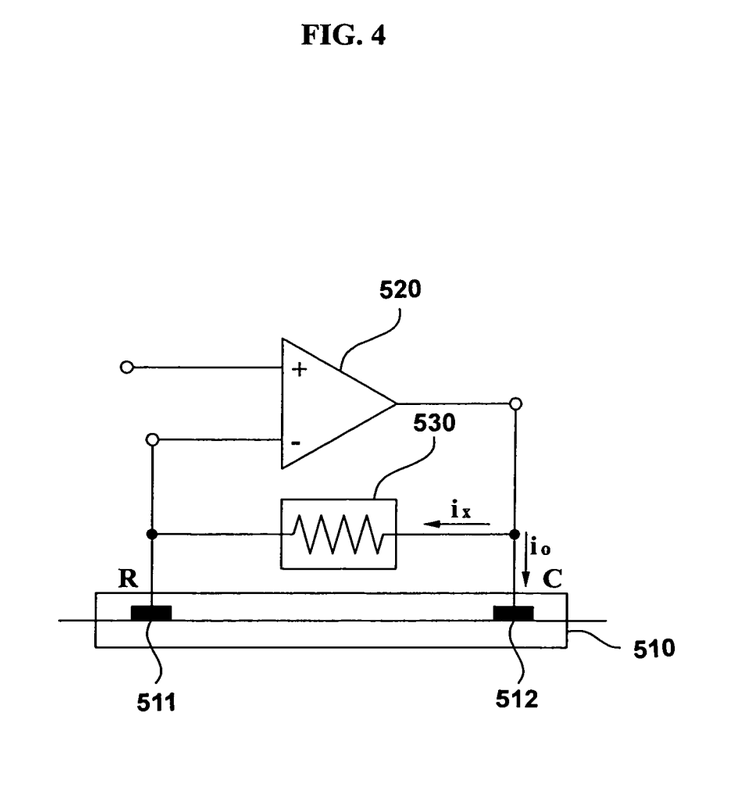
FIG. 4 illustrates a circuit configuration of an apparatus to measure skin moisture content according to a second embodiment of the present invention.

FIG. 4 illustrates a circuit configuration of an apparatus to measure skin moisture content according to a second embodiment of the present invention.

The apparatus to measure skin moisture content according to the present embodiment includes an electrode unit 510, an operational amplifier 520, and a resistor 530.

The electrode unit 510 includes an R electrode 511, a C electrode 512, and an M electrode (not shown). The electrode unit may be constructed to include the R electrode 511, the C electrode 512, and the M electrode. Also, the electrode unit 510 may be constructed to include any type of electrode that can measure the skin moisture content.

An inverting input terminal of the operational amplifier 520 connects with the R electrode 511, and an output terminal of the operational amplifier 520 connects with the C electrode 512.

The resistor 530 connects with the R electrode 511 and the C electrode 512. Specifically, the resistor 530 connects the inverting input terminal and the output terminal of the operational amplifier 520 via the connection between the R electrode 511 and the C electrode 512, so that the operational amplifier 520 may form a loop.

Also, the resistor 530 may be designed to have a resistance value of at least 1 MΩ. In this case, current $i_x$ flows via the resistor 530 before the electrode unit 510 contacts with the skin of a user, i.e. in a measurement standby mode. Although the resistor 530 has the resistance value of at least 1 MΩ, the current $i_x$ includes a comparatively smaller amount of current in comparison to current flowing when the resistor 530 is not provided and thus an infinite load is formed in the C electrode 512. Also, when the current $i_x$ flows via the resistor 530, current does not flow into the C electrode 512.

Also, skin impedance generally has a resistance value of tens to millions of KΩ. Therefore, when the electrode unit 510 contacts with the skin of the user and thereby starts measuring the skin moisture content from the skin of the user, the resistance value of the resistor 530 is comparatively greater than the resistance value of the skin of the user. Accordingly, output current $i_o$ of the operational amplifier 520 mostly flows into the C electrode 512.

As described above, according to the second embodiment, by only connecting the R electrode 511 and the C electrode 512, and designing the resistor 530 to have the resistance value of at least 1 MΩ, it is possible to reduce power consumption in the measurement standby mode.

Figure 5:
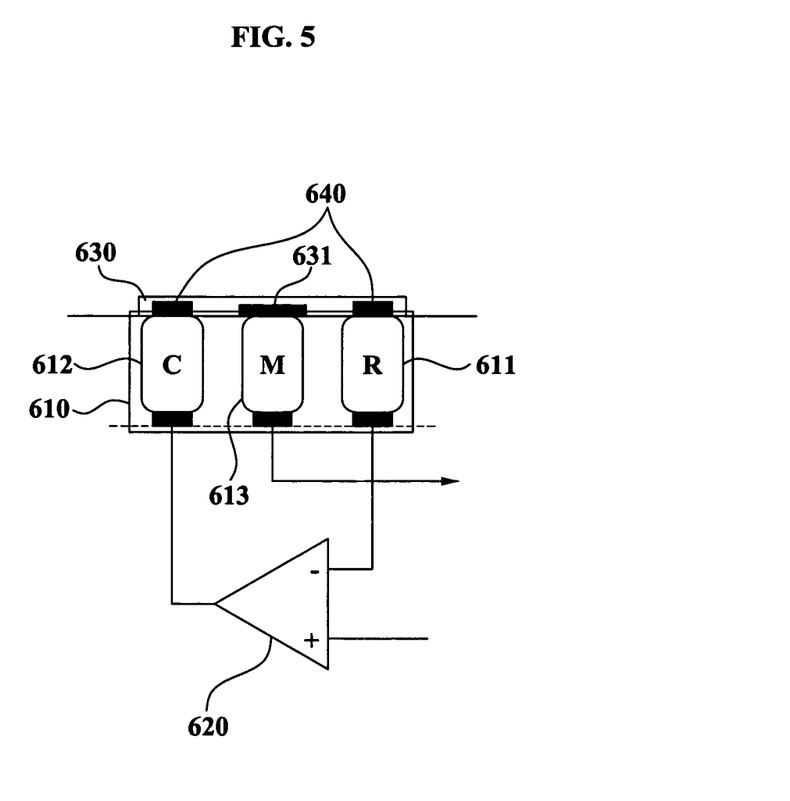
FIG. 5 illustrates a configuration of an apparatus to measure skin moisture content when a member is closed according to a 3-1 embodiment of the present invention.

FIG. 5 illustrates a configuration of an apparatus to measure skin moisture content when a member is closed according to a 3-1 embodiment of the present invention.

The apparatus for measuring skin moisture content according to the present embodiment includes an electrode unit 610, an operational amplifier 620, and a member 630.

The electrode unit 610 includes an R electrode 611, a C electrode 612, and an M electrode 613. The electrode unit 610 may be constructed to include the R electrode 611, the C electrode 612, and the M electrode 613. Also, the electrode unit 610 may be constructed to include any type of electrode that can measure the skin moisture content.

An inverting input terminal of the operational amplifier 620 connects with the R electrode 611, and an output terminal of the operational amplifier 620 connects with the C electrode 612.

The member 630 is provided to contact with the R electrode 611, the C electrode 612, and the M electrode 613. Specifically, as shown in FIG. 5, the member 630 may be formed in a type of a cover to open and close the electrode unit.

The member 630 includes a conductor 640 and an insulator 631. In this instance, inside of the member 630 and a portion of the member 630 contacting with the R electrode 611 and the C electrode 612 may include the conductor 640. Also, a portion of the member 630 contacting with the M electrode 613 may include the insulator 631.

When the member 630 is closed to cover the electrode unit 610 in a measurement standby mode, the conductor 640 electrically connects the R electrode 611 and the C electrode 612, and the insulator 631 electrically isolates the M electrode 613.

As described above, when the R electrode 611 and the C electrode 612 electrically connect with each other via the conductor of the member 630, the operational amplifier 620 forms a loop connecting an output terminal and an inverting input terminal of the operational amplifier 620. Accordingly, theoretically, no current flow exists and in actuality, only a minute current may flow and thus it is possible to reduce power consumption in the measurement standby mode.

Figure 6:
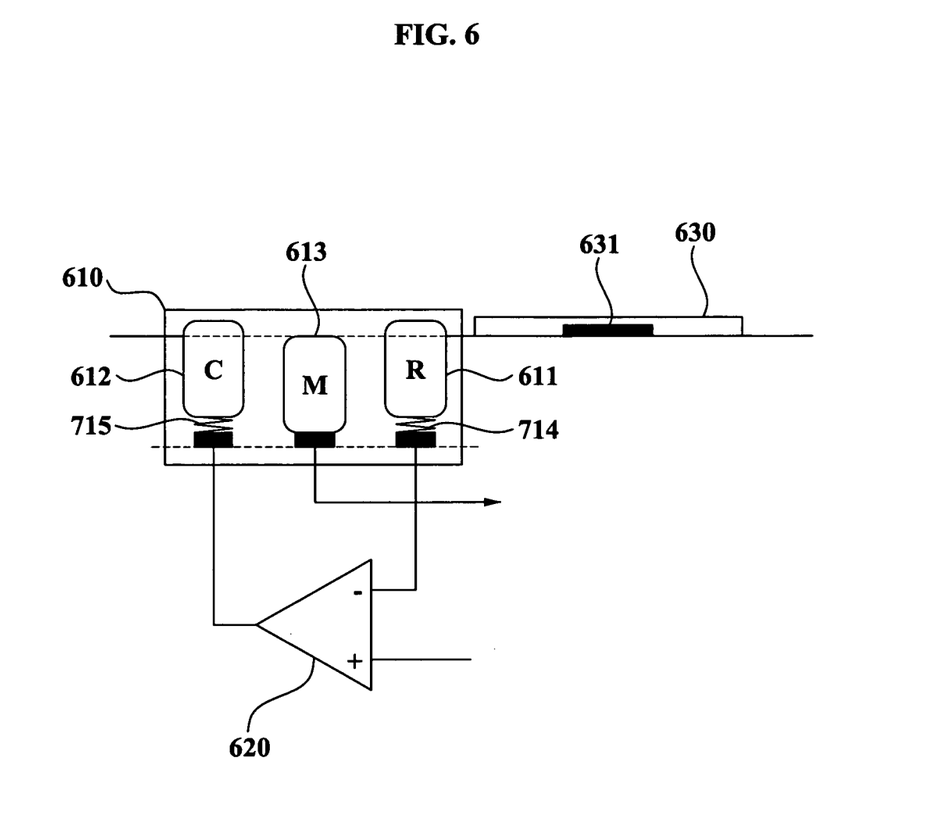
FIG. 6 illustrates a configuration of an apparatus to measure skin moisture content when a member is opened according to a 3-1 embodiment of the present invention.

FIG. 6 illustrates a configuration of an apparatus to measure skin moisture content when a member is opened according to a 3-1 embodiment of the present invention.

In the apparatus to measure skin moisture content shown in FIG. 6, a member 630 is opened and thereby an electrode unit is spaced apart from the member 630.

As described above, when the member 630 is opened to measure the skin moisture content from the skin of a user, the member 630 makes no contact with an R electrode 611, a C electrode 612, and an M electrode 613, and thus a connection between an insulator 631 and the M electrode 613 is also released.

Accordingly, when the member 630 is opened, the electrical connection between the R electrode 611 and the C electrode 612 is also released. Also, as the R electrode 611, the C electrode 612, and the M electrode 613 contact with the skin of the user, the apparatus to measure skin moisture content may measure the skin moisture content from the skin of the user.

Elastic devices 714 and 715 may be provided to the R electrode 611 and the C electrode 612 respectively. When the member 630 is opened, the R electrode 611 and the C electrode 612 move towards the skin of the user according to the elastic motion of the elastic devices 714 and 715, and thereby contact with the skin of the user with a stepped pulley with respect to the M electrode 613. Accordingly, it is possible to accurately measure the skin moisture content from the skin of the user.

Figure 7:
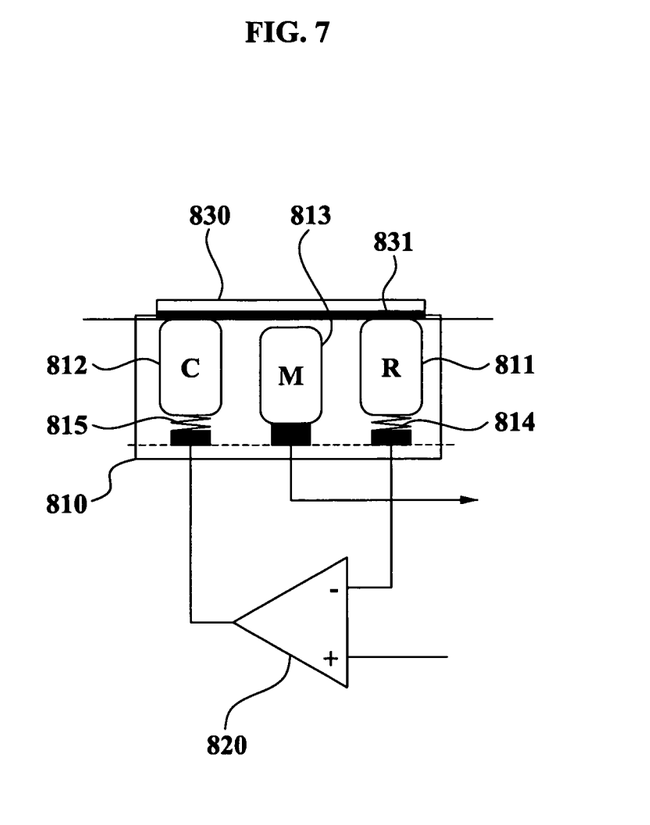
FIG. 7 illustrates a configuration of an apparatus to measure skin moisture content when a member is closed according to a 3-2 embodiment of the present invention.

FIG. 7 illustrates a configuration of an apparatus to measure skin moisture content when a member is closed according to a 3-2 embodiment of the present invention.

The apparatus to measure skin moisture content according to the present embodiment includes an electrode unit 810, an operational amplifier 820, and a member 830.

The electrode unit 810 includes an R electrode 811, a C electrode 812, and an M electrode 813. Specifically, the electrode unit may be constructed to include the R electrode 811, the C electrode 812, and the M electrode 813. Also, the electrode unit may be constructed to include any type of electrode that can measure the skin moisture content.

Also, the M electrode 813 may be designed to have a stepped pulley with respect to the R electrode 811 and the C electrode 812. As shown in FIG. 7, the M electrode 813 may be formed in a concave shape with respect to the R electrode 811 and the C electrode 812. Also, elastic devices 814 and 815 may be provided to the R electrode 811 and the C electrode 812 respectively.

An inverting input terminal of the operational amplifier 820 connects with the R electrode 811, and an output terminal of the operational amplifier 820 connects with the C electrode 812.

The member 830 contacts with the R electrode 811 and the C electrode 812. Specifically, as shown in FIG. 7, the member 830 may be formed in a type of a cover to open and close the electrode unit. In this instance, since the M electrode 813 includes the stepped pulley with respect to the R electrode 811 and the C electrode 812, the M electrode 813 makes no contact with the member 830.

A conductor 831 may be included inside the member 830 and a portion of the member 830 contacting with the R electrode 811 and the C electrode 812. Specifically, when the member 830 is closed to cover the electrode unit 810 in a measurement standby mode, the conductor 831 may electrically connect the R electrode 811 and the C electrode 812.

As described above, when the R electrode 811 and the C electrode 812 electrically connect with each other via the conductor of the member 830, the operational amplifier 820 forms a loop connecting an output terminal and an inverting input terminal of the operational amplifier 820. Accordingly, theoretically, no current flow exists and in actuality, only a minute current may flow and thus it is possible to reduce power consumption in the measurement standby mode.

Figure 8:
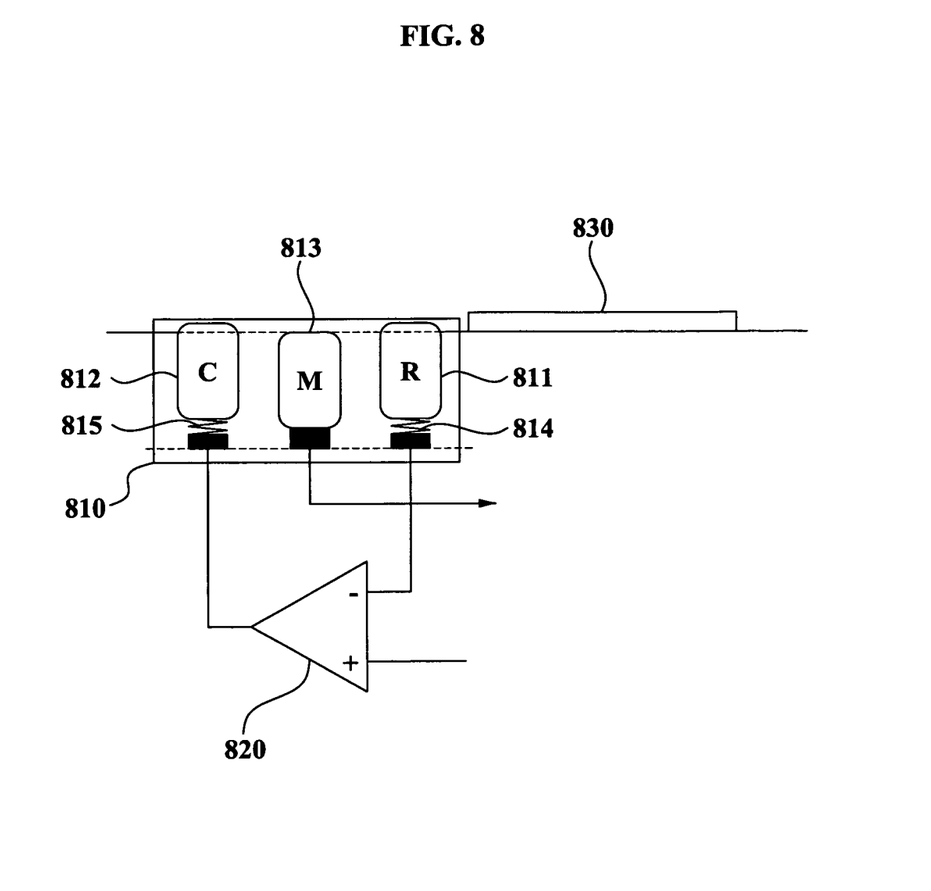
FIG. 8 illustrates a configuration of an apparatus to measure skin moisture content when a member is opened according to a 3-2 embodiment of the present invention.

FIG. 8 illustrates a configuration of an apparatus to measure skin moisture content when a member is open according to the 3-2 embodiment of the present invention.

In the apparatus to measure skin moisture content shown in FIG. 8, a member 830 is opened and thus an electrode unit is spaced apart from the member 830.

As described above, when the member 830 is opened to measure the skin moisture content from the skin of a user, the member 830 makes no contact with an R electrode 811, a C electrode 812, and an M electrode 813. Accordingly, when the member 830 is opened, the electrical connection between the R electrode 811 and the C electrode 812 is also released. Also, as the R electrode 811, the C electrode 812, and the M electrode 813 contact with the skin of the user, the apparatus to measure skin moisture content may measure the skin moisture content from the skin of the user.

Elastic devices 814 and 815 may be provided to the R electrode 811 and the C electrode 812 respectively. When the member 830 is opened, the R electrode 811 and the C electrode 812 move towards the skin of the user according to the elastic motion of the elastic devices 814 and 815, and thus contact with the skin of the user with a stepped pulley with respect to the M electrode 813. Accordingly, it is possible to accurately measure the skin moisture content from the skin of the user.

As described above with reference to FIGS. 3 through 8, the apparatus to measure skin moisture content according to each of the first embodiment, the second embodiment, the 3-1 embodiment and the 3-2 embodiment of the present invention may electrically connect an R electrode and an C electrode in a measurement standby mode, and may release the electrical connection between the R electrode and the C electrode while the skin moisture content is measured. Specifically, since an inverting input terminal and an output terminal of an operational amplifier form a loop depending on the electrical connection between the R electrode and the C electrode, it is possible to reduce power consumption in the measurement standby mode.

According to the above-described exemplary embodiments of the present invention, there is provided an apparatus to measure skin moisture content, which can connect an R electrode and a C electrode via a switch, and control the switch to connect the R electrode and the C electrode in a standby mode to measure the skin moisture content, and also control the switch to release the connection between the R electrode and the C electrode while the skin moisture content is measured from the skin of a user, and thereby can reduce power consumption in the standby mode.

Also, according to the above-described exemplary embodiments of the present invention, there is provided an apparatus to measure skin moisture content, which can connect an R electrode and a C electrode via a resistor and thereby can reduce power consumption in a measurement standby mode. In this instance, the resistor has a comparatively greater resistance value in comparison to stratum corneum.

Also, according to the above-described exemplary embodiments of the present invention, there is provided an apparatus to measure skin moisture content, which can design a member to be opened and closed, so that a conductor of the member may contact with an R electrode and a C electrode and an insulator of the member may contact with an M electrode in a measurement standby mode, and thereby can reduce power consumption. In this instance, the member connects the R electrode and the C electrode via the conductor, and contacts with the M electrode via the insulator.

Also, according to the above-described exemplary embodiments of the present invention, there is provided an apparatus to measure skin moisture content, which can design an M electrode to have a stepped pulley with respect to an R electrode and a C electrode, and design a member to be opened and closed, so that a conductor of the member may contact with the R electrode and the C electrode in a measurement standby mode, and thereby can reduce power consumption. In this instance, the member connects the R electrode and the C electrode via the conductor.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. An apparatus to measure skin moisture content, the apparatus comprising:
    an electrode unit comprising a reference (R) electrode, a current (C) electrode, and a measuring (M) electrode;
    an operational amplifier having an inverting input terminal connect with the R electrode, and having an output terminal connect with the C electrode;
    a first switch connecting the R electrode and the C electrode when the electrode unit is in a standby mode, and releasing a connection between the R electrode and the C electrode when the electrode unit is in a measurement mode; and
    a microcontroller controlling the connection between the R electrode and the C electrode via the first switch.

2. The apparatus of claim 1, further comprising:
    a second switch connecting the C electrode and the operational amplifier when the electrode unit is in the measurement mode.

3. The apparatus of claim 2, wherein the microcontroller controls the first switch to maintain the connection between the R electrode and the C electrode while the second switch releases the connection between the C electrode and the operational amplifier, and the microcontroller controls the first switch to release the connection between the R electrode and the C electrode while the second switch maintains the connection between the C electrode and the operational amplifier.

4. The apparatus of claim 1, wherein the R electrode, C electrode, and M electrode further comprises elastic devices.

5. The apparatus of claim 2, wherein the second switch is an elastic switch.

6. An apparatus to measure skin moisture content, the apparatus comprising:
    an electrode unit comprising an R electrode, a C electrode, and an M electrode;
    an operational amplifier having an inverting input terminal connect with the R electrode, and having an output terminal connect with the C electrode; and
    a member comprising a conductor contacting with the R electrode and the C electrode, and an insulator contacting with the M electrode,
    wherein the member is designed to be opened and closed, and the member is opened to release the connection between the conductor and the R electrode and the C electrode, and the connection between the M electrode and the insulator, when the skin moisture content is measured from the skin of a user.

7. An apparatus to measure skin moisture content, the apparatus comprising:
    an electrode unit comprising an R electrode, a C electrode, and an M electrode, the M electrode comprising a stepped pulley with respect to the R electrode and the C electrode;
    an operational amplifier having an inverting input terminal connect with the R electrode, and having an output terminal connect with the C electrode; and
    a member comprising a conductor contacting with the R electrode and the C electrode,
    wherein the member is designed to be opened and closed, and the member is opened to release the connection between the conductor and the R electrode and the C electrode when the skin moisture content is measured from the skin of a user.

8. The apparatus of claim 7, wherein the electrode unit further comprises elastic devices are provided to the R electrode and the C electrode.

* * * * *